(12) United States Patent
Simpson et al.

(10) Patent No.: US 9,352,135 B2
(45) Date of Patent: *May 31, 2016

(54) METHOD FOR FORMING CATHETER BALLOON

(71) Applicant: Abbott Cardiovascular Systems Inc., Santa Clara, CA (US)

(72) Inventors: John A. Simpson, Carlsbad, CA (US); Sarah A. Nelson, New Haven, CT (US); Jonathan P. Durcan, Temecula, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 148 days.

This patent is subject to a terminal disclaimer.

(21) Appl. No.: 14/204,885

(22) Filed: Mar. 11, 2014

(65) Prior Publication Data

US 2014/0190630 A1    Jul. 10, 2014

Related U.S. Application Data

(63) Continuation of application No. 12/881,733, filed on Sep. 14, 2010, now Pat. No. 8,703,260.

(51) Int. Cl.
*A61M 25/10* (2013.01)
*A61L 29/04* (2006.01)
(Continued)

(52) U.S. Cl.
CPC ............ *A61M 25/1029* (2013.01); *A61L 29/04* (2013.01); *A61L 29/14* (2013.01); *A61M 25/0009* (2013.01); *B29C 49/185* (2013.01); *B29C 49/22* (2013.01); *A61F 2/958* (2013.01); *A61L 2420/08* (2013.01); *A61M 25/104* (2013.01); *A61M 2025/1075* (2013.01);

(Continued)

(58) Field of Classification Search
CPC ...... B29C 49/185; B29C 49/22; B29C 49/04; A61M 25/0009; A61M 25/104; A61M 25/1029; Y10T 428/1352; Y10T 428/139; Y10T 428/1393
See application file for complete search history.

(56) References Cited

U.S. PATENT DOCUMENTS

| 4,952,357 A | 8/1990 | Euteneuer |
| 5,112,304 A | 5/1992 | Barlow et al. |

(Continued)

FOREIGN PATENT DOCUMENTS

| EP | 0420488 | 3/1991 |
| EP | 0485903 | 10/1996 |

(Continued)

OTHER PUBLICATIONS

U.S. Appl. No. 11/313,041, Oct. 4, 2010 Issue Fee payment.

(Continued)

*Primary Examiner* — Walter B Aughenbaugh
(74) *Attorney, Agent, or Firm* — Baker Botts L.L.P.

(57) ABSTRACT

Method of making a balloon catheter includes providing an elongated shaft having a proximal end and a distal end and an inflation lumen extending therein, providing a multilayer tube, forming a multilayer balloon by blow-molding the multilayer tube such that the multilayer balloon is blown, in at least a first stage, to a final working radial dimension, and securing the multilayer balloon on a distal section of the shaft with an interior of the multilayer balloon in fluid communication with the inflation lumen. The ADDR of the multilayer balloon after formation is approximately 2.0.

18 Claims, 5 Drawing Sheets

(51) Int. Cl.
*A61L 29/14* (2006.01)
*B29C 49/18* (2006.01)
*B29C 49/22* (2006.01)
*A61M 25/00* (2006.01)
*A61F 2/958* (2013.01)
*B29C 49/04* (2006.01)
*B29L 31/00* (2006.01)

(52) U.S. Cl.
CPC ......... *B29C49/04* (2013.01); *B29L 2031/7543* (2013.01); *Y10T 428/1334* (2015.01); *Y10T 428/1352* (2015.01); *Y10T 428/1386* (2015.01); *Y10T 428/1393* (2015.01)

(56) References Cited

U.S. PATENT DOCUMENTS

| | | |
|---|---|---|
| 5,195,969 A | 3/1993 | Wang et al. |
| 5,207,700 A | 5/1993 | Euteneuer |
| 5,270,086 A | 12/1993 | Hamlin |
| 5,290,306 A | 3/1994 | Trotta et al. |
| 5,358,486 A | 10/1994 | Saab |
| 5,447,497 A | 9/1995 | Sogard et al. |
| 5,478,320 A | 12/1995 | Trotta |
| 5,499,980 A | 3/1996 | Euteneuer |
| 5,512,051 A | 4/1996 | Wang et al. |
| 5,556,383 A | 9/1996 | Wang et al. |
| 5,587,125 A | 12/1996 | Roychowdhury |
| 5,613,979 A | 3/1997 | Trotta et al. |
| 5,620,649 A | 4/1997 | Trotta |
| 5,647,848 A | 7/1997 | Jorgensen |
| 5,679,817 A | 10/1997 | Sakai et al. |
| 5,755,690 A | 5/1998 | Saab |
| 5,769,817 A | 6/1998 | Burgmeier |
| 5,797,887 A | 8/1998 | Rosen et al. |
| 5,807,327 A | 9/1998 | Green et al. |
| 5,833,657 A | 11/1998 | Reinhardt et al. |
| 5,879,369 A | 3/1999 | Ishida |
| 5,908,406 A | 6/1999 | Ostapchenko et al. |
| 6,004,289 A | 12/1999 | Saab |
| 6,004,339 A | 12/1999 | Wijay |
| 6,024,722 A | 2/2000 | Rau et al. |
| 6,059,751 A | 5/2000 | Ostapchenko et al. |
| 6,086,556 A | 7/2000 | Hamilton et al. |
| 6,124,007 A | 9/2000 | Wang et al. |
| 6,132,824 A | 10/2000 | Hamlin |
| 6,136,258 A | 10/2000 | Wang et al. |
| 6,146,356 A | 11/2000 | Wang et al. |
| 6,171,278 B1 | 1/2001 | Wang et al. |
| 6,242,063 B1 | 6/2001 | Ferrera et al. |
| 6,328,925 B1 | 12/2001 | Wang et al. |
| 6,358,227 B1 | 3/2002 | Ferrera et al. |
| 6,416,494 B1 | 7/2002 | Wilkins |
| 6,495,090 B1 | 12/2002 | Wilkins |
| 6,500,148 B1 | 12/2002 | Pinchuk et al. |
| 6,585,688 B2 | 7/2003 | Ferrera et al. |
| 6,620,127 B2 | 9/2003 | Lee et al. |
| 6,620,128 B1 | 9/2003 | Simhambhatla |
| 6,645,422 B2 | 11/2003 | Jung et al. |
| 6,673,302 B2 | 1/2004 | Wang et al. |
| 6,695,809 B1 | 2/2004 | Lee |
| 6,756,094 B1 | 6/2004 | Wang et al. |
| 6,796,960 B2 | 9/2004 | Cioanta et al. |
| 6,835,189 B2 | 12/2004 | Musbach et al. |
| 6,866,650 B2 | 3/2005 | Stevens et al. |
| 6,875,197 B1 | 4/2005 | Simhambhatla et al. |
| 6,896,842 B1 | 5/2005 | Hamilton et al. |
| 6,911,038 B2 | 6/2005 | Mertens et al. |
| 6,946,092 B1 | 9/2005 | Bertolino et al. |
| 6,949,112 B1 | 9/2005 | Sridharan et al. |
| 6,951,675 B2 | 10/2005 | Chin et al. |
| 7,026,026 B2 | 4/2006 | Ferrera et al. |
| 7,029,732 B2 | 4/2006 | Wang et al. |
| 7,074,206 B2 | 7/2006 | Lee et al. |
| 7,112,357 B2 | 9/2006 | Miller et al. |
| 7,147,817 B1 | 12/2006 | Lim et al. |
| 7,195,638 B1 | 3/2007 | Sridharan et al. |
| 7,335,185 B2 | 2/2008 | Tang et al. |
| 7,781,038 B2 | 8/2010 | Hamilton et al. |
| 7,815,628 B2 | 10/2010 | Devens, Jr. |
| 7,828,766 B2 | 11/2010 | Durcan et al. |
| 7,906,066 B2 | 3/2011 | Wilson et al. |
| 7,942,847 B2 | 5/2011 | Stupecky et al. |
| 8,388,575 B2 | 3/2013 | Durcan et al. |
| 8,394,055 B2 | 3/2013 | Durcan et al. |
| 8,703,260 B2 * | 4/2014 | Simpson ................ A61L 29/04 264/234 |
| 9,095,689 B2 | 8/2015 | Durcan |
| 2002/0018866 A1 | 2/2002 | Lee et al. |
| 2002/0087165 A1 | 7/2002 | Lee et al. |
| 2002/0118866 A1 | 8/2002 | Breeuwer et al. |
| 2002/0165523 A1 | 11/2002 | Chin et al. |
| 2002/0171180 A1 | 11/2002 | Simhambhatla |
| 2004/0096606 A1 | 5/2004 | Lee et al. |
| 2004/0170782 A1 | 9/2004 | Wang et al. |
| 2004/0173935 A1 | 9/2004 | Lim et al. |
| 2004/0191443 A1 | 9/2004 | Hamlin |
| 2005/0043679 A1 | 2/2005 | Devens et al. |
| 2005/0124976 A1 | 6/2005 | Devens, Jr. et al. |
| 2005/0186370 A1 | 8/2005 | Hamilton et al. |
| 2005/0228429 A1 | 10/2005 | Burgmeier et al. |
| 2005/0238833 A1 | 10/2005 | Wang et al. |
| 2005/0277878 A1 | 12/2005 | Lee |
| 2006/0165926 A1 | 7/2006 | Weber |
| 2007/0060863 A1 | 3/2007 | Goeken et al. |
| 2007/0142771 A1 | 6/2007 | Durcan |
| 2007/0142772 A1 | 6/2007 | Deshmukh et al. |
| 2007/0167973 A1 | 7/2007 | Stupecky et al. |
| 2007/0250101 A1 | 10/2007 | Horn et al. |
| 2008/0045928 A1 | 2/2008 | Simpson et al. |
| 2008/0065188 A1 | 3/2008 | Pallazza |
| 2009/0156998 A1 | 6/2009 | Arana et al. |
| 2010/0010470 A1 | 1/2010 | Bates |
| 2011/0022150 A1 | 1/2011 | Durcan et al. |
| 2012/0065718 A1 | 3/2012 | Simpson et al. |
| 2012/0145317 A1 | 6/2012 | Durcan et al. |
| 2012/0203324 A1 | 8/2012 | Durcan |
| 2013/0172817 A1 | 7/2013 | Durcan et al. |
| 2014/0142505 A1 | 5/2014 | Lin et al. |
| 2014/0190630 A1 | 7/2014 | Simpson et al. |

FOREIGN PATENT DOCUMENTS

| | | |
|---|---|---|
| EP | 0611576 | 1/1997 |
| EP | 0 768 097 | 4/1997 |
| EP | 0592885 | 7/2009 |
| JP | H05-305146 | 11/1993 |
| JP | H06-507101 | 8/1994 |
| JP | 2001/1029450 | 2/2001 |
| JP | 2005-167638 | 6/2005 |
| JP | 2007/000157 | 1/2007 |
| WO | WO 92/08512 | 5/1992 |
| WO | WO 95/18647 | 7/1995 |
| WO | WO 01/51115 | 7/2001 |
| WO | WO 02/056930 | 7/2002 |
| WO | WO 2005/021083 | 3/2005 |
| WO | WO 2005/065735 | 7/2005 |
| WO | WO2006126311 | 11/2006 |

OTHER PUBLICATIONS

U.S. Appl. No. 11/313,041, Jul. 2, 2010 Notice of Allowance.
U.S. Appl. No. 11/313,041, Jun. 4, 2010 Request for Continued Examination (RCE).
U.S. Appl. No. 11/313,041, Apr. 6, 2010 Notice of Allowance.
U.S. Appl. No. 11/313,041, Mar. 1, 2010 Amendment and Request for Continued Examination (RCE).
U.S. Appl. No. 11/313,041, Oct. 27, 2009 Final Office Action.
U.S. Appl. No. 11/313,041, Jun. 22, 2009 Response to Non-Final Office Action.
U.S. Appl. No. 11/313,041, Apr. 17, 2009 Examiner Interview Summary.
U.S. Appl. No. 11/313,041, Jan. 22, 2009 Non-Final Office Action.

(56) References Cited

OTHER PUBLICATIONS

U.S. Appl. No. 11/313,041, Dec. 8, 2008 Amendment and Request for Continued Examination (RCE).
U.S. Appl. No. 11/313,041, Sep. 16, 2008 Final Office Action.
U.S. Appl. No. 11/313,041, May 12, 2008 Response to Non-Final Office Action.
U.S. Appl. No. 11/313,041, Feb. 21, 2008 Non-Final Office Action.
U.S. Appl. No. 12/897,202, Feb. 7, 2013 Issue Fee payment.
U.S. Appl. No. 12/897,202, Nov. 7, 2012 Notice of Allowance.
U.S. Appl. No. 13/397,140, May 17, 2013 Notice of Allowance.
U.S. Appl. No. 13/397,140, Feb. 26, 2013 Response to Non-Final Office Action.
U.S. Appl. No. 13/397,140, Oct. 26, 2012 Non-Final Office Action.
U.S. Appl. No. 13/447,635, Feb. 5, 2013 Issue Fee payment.
U.S. Appl. No. 13/447,635, Nov. 5, 2012 Notice of Allowance.
U.S. Appl. No. 12/881,733, Dec. 4, 2013 Notice of Allowance.
U.S. Appl. No. 12/881,733, Oct. 30, 2013 Response to Non-Final Office Action.
U.S. Appl. No. 12/881,733, Oct. 17, 2013 Applicant-Initiated Interview Summary.
U.S. Appl. No. 12/881,733, Sep. 24, 2013 Applicant-Initiated Interview Summary.
U.S. Appl. No. 12/881,733, May 30, 2013 Non-Final Office Action.
U.S. Appl. No. 12/881,733, Mar. 12, 2013 Response to Restriction Requirement.
U.S. Appl. No. 12/881,733, Feb. 12, 2013 Restriction Requirement.
U.S. Appl. No. 13/680,299, Nov. 10, 2014 Response to Restriction Requirement.
U.S. Appl. No. 13/680,299, Sep. 8, 2014 Restriction Requirement.
U.S. Appl. No. 13/775,724, Nov. 20, 2014 Non-Final Office Action.
Material Testing Analysis & Characterization of Traytuf 7357 (5 pages) 2007 (month and date are not available).
Nylon Plastics Handbook, Melvin I. Kohan 1995, pp. 298-302 (month and date are not available).
Thesis for the Degree of Master of Science by Samantha Garramone, (65 pages) 2001 (month and date are not available).
Concise Encyclopedia of Polymer Science and Engineering, p. 759, 815, 1990 (month and date are not available).
("Hytrel" data sheet) including Hytrel TPC-ET, (94 pages), date not available.
DuPont Product Information, "Hytrel polyester elastomer", Nov. 1993 (date is not available).
DuPont Product Information, Injection Molding Guide, "Hytrel polyester elastomer", Oct. 1996 (date is not available).
DuPont Engineering Polymers, "From concept to commercialisation," (40 pages) Sep. 1996 (date is not available).
DuPont Product and Properties Guide, "Hytrel polyester elastomer" Nov. 1999 (date is not available).
Data Sheets of Hytrel grades (2 pages), date not available.
Table "Hytrel grades available before Oct. 1996" (date is not available).
Mat Web Information for Plexar (25 pages) Accessed Oct. 20, 2008.
"Synthesis and characterization of hyperbranched polyglycerol hydrogels," Oudshoorn et al., Biomaterials, 27:5471-5479, Jul. 2006 (date is not available).
Ahearne, et al., "Mechanical characterisation of hydrogels for tissue engineering applications," Topics in Tissue Engineering, 4 (Chapter 12): 3-16, 2008 (month and date are not available).
Technical data sheet "Traytuf® 7357 Polyester Resin", date not available.
Technical data sheet "Selar PT 4368" Oct. 31, 1990.
Affidavit of Dr. John Chen regarding the measurements for Traytuf 7357 mentioned in Material Testing analysis & Characterization of Traytuf 7357. 2009 (month and date are not available).
"Comparison of Arnitel EL 740 With Hytrel 7246", retrieved from co-pending application U.S. Appl. No. 11/313,041 on Apr. 1, 2013.
"Cleartuf 8006", Shell Chemical Company. date not available.
Extract from Wikipedia, "Polyimide" (2 sheets) 2009 (month and date are not available).
Data sheet Aurum PL450C (2 sheets), received Oct. 19, 2009.
International Search Report dated Jul. 23, 2014 in PCT/US2013/070540.
U.S. Appl. No. 14/443,805, filed May 19, 2015.
U.S. Appl. No. 14/748,376, filed Jun. 24, 2015.
U.S. Appl. No. 14/820,664, filed Aug. 7, 2015.
U.S. Appl. No. 13/397,140, Aug. 16, 2013 Issue Fee Payment.
U.S. Appl. No. 12/881,733, Mar. 4, 2014 Issue Fee Payment.
U.S. Appl. No. 13/680,299, Aug. 7, 2015 Issue Fee Payment.
U.S. Appl. No. 13/680,299, May 8, 2015 Notice of Allowance.
U.S. Appl. No. 13/680,299, Feb. 24, 2015 Response to Non-Final Office Action.
U.S. Appl. No. 13/680,299, Nov. 26, 2014 Non-Final Office Action.
U.S. Appl. No. 13/775,724, Feb. 20, 2015 Response to Non-Final Office Action.
U.S. Appl. No. 13/775,724, Feb. 26, 2015 Applicant Initiated Interview Summary.
U.S. Appl. No. 13/775,724, Mar. 24, 2015 Noticed of Allowance.
U.S. Appl. No. 13/775,724, Jun. 24, 2015 Issue Fee Payment.
U.S. Appl. No. 13/775,724, Aug. 5, 2015 Notice of Allowance.
U.S. Appl. No. 13/775,724, Oct. 6, 2015 Non-Final Office Action.

* cited by examiner

AS-EXTRUDED TUBING, N=10 ELEMENTS

FIG. 7

EXPANDED BALLON WALL, N=10 ELEMENTS

METHOD FOR FORMING CATHETER BALLOON

CROSS-REFERENCE TO RELATED APPLICATION

This application is a continuation of U.S. patent application Ser. No. 12/881,733, entitled "Catheter Balloon and Method of Forming Same," filed Sep. 14, 2010, the contents of which are fully incorporated herein by reference.

BACKGROUND

The invention relates to the field of intravascular medical devices, and more particularly to an improved balloon for a catheter.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion or obstruction to be dilated. The dilatation catheter having an inflatable balloon on the distal portion thereof is then advanced into the patient's coronary anatomy, over the previously introduced guidewire, until the balloon of the dilatation catheter is properly positioned across the lesion or obstruction. Once properly positioned, the dilatation balloon is inflated with liquid one or more times to a predetermined size at relatively high pressures (e.g., greater than 8 atmospheres) so that the stenosis is compressed against the arterial wall and the wall expanded to open up the passageway. Generally, the inflated diameter of the balloon is approximately the same diameter as the native diameter of the body lumen being dilated so as to effect the dilatation without over-expanding the arterial wall. Substantial, uncontrolled expansion of the balloon against the vessel wall can cause trauma to the vessel wall. After the balloon is finally deflated, blood flow may resume through the dilated artery and the dilatation catheter can be withdrawn from the patient.

In such angioplasty procedures, there may be restenosis of the artery, i.e. reformation of the arterial blockage, or obstructions that cannot be resolved by inflation of the balloon alone. These conditions often necessitate either another angioplasty procedure, or some other method of repairing, strengthening, or unblocking the dilated area. To reduce the restenosis rate and to strengthen or unblock the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter and expanded to a larger diameter by expansion of the balloon. The balloon is deflated to remove the catheter and the stent left in place within the artery at the site of the dilated lesion.

Catheter balloons are typically manufactured independently of the catheter itself and then secured to the catheter with an adhesive or other bonding method. In standard balloon manufacture, a polymer tube is blown biaxially under the action of axial tension, internal pressure, and heat within a mold. The polymer tube may either be simultaneously stretched in the radial and axial directions, or sequentially by first stretching axially and then radially. The starting dimensions of the polymer tube and the finished dimensions of the blow-molded balloon within the mold are a measure of the degree to which the polymeric material has been stretched and oriented during balloon blowing, and affect important characteristics of the finished balloon such as rupture pressure and compliance. The blow-up-ratio (BUR) refers generally to the ratio of the diameter of the blown balloon to the diameter of the undeformed polymer tube. Above a critical BUR for a selected polymer, the balloon blowing process becomes unstable and the polymer tubing will rupture or tear before a balloon is fully formed.

In the standard blow molding process, an initiated air bubble in the polymer tube rapidly expands until the polymer tube forms a balloon that is eventually constrained by the mold wall. The hoop stress in the wall of the tubing, as it grows into a balloon, may be approximated by the expression:

$$\sigma_h = (P \cdot R)/\delta$$

where P is the inflation pressure, R is the mean radius of the polymeric tube at any time during the inflation and $\delta$ is the wall thickness of the tubing. To form a balloon from the tubing, the inflation pressure P should be such that the wall hoop stress exceeds the material resistance (typically the yield stress) to stretching at the blowing temperature. Once a balloon begins to form from the tubing, it grows rapidly in size until it touches the mold wall. As the balloon expands, its radius R increases and its wall thickness $\delta$ decreases. This results in a rapid increase in the wall hoop stress $\sigma_h$ during constant pressure blowing. If the wall hoop stress of the growing balloon exceeds the ultimate hoop strength of the material, rupture will occur. This phenomena limits the maximum attainable BUR for a given polymeric material forming the balloon layer.

In the design of catheter balloons, balloon characteristics such as strength, flexibility and compliance must be tailored to provide optimal performance for a particular application. Angioplasty and stent delivery balloons preferably have high strength for inflation at relatively high pressure, and high flexibility and softness for improved ability to track the tortuous anatomy and cross lesions. The balloon compliance is chosen so that the balloon will have the required amount of expansion during inflation. Compliant balloons, for example balloons made from materials such as polyethylene, exhibit substantial stretching upon the application of internal pressure. Noncompliant balloons, for example balloons made from materials such as PET, exhibit relatively little stretching during inflation, and therefore provide controlled radial growth in response to an increase in inflation pressure within the working pressure range. However, noncompliant balloons generally have relatively low flexibility and softness, making it challenging to provide a low compliance balloon with high flexibility and softness for enhanced catheter trackability. A compromise is typically struck between the competing considerations of softness/flexibility and noncompliance, which, as a result, has limited the degree to which the compliance of catheter balloons can be further lowered.

As a balloon is formed by the process described above where an extruded tube is expanded into a mold cavity, the balloon's wall always exhibits a gradient in circumferential orientation of the polymer molecules within. Moreover, the highest degree of orientation occurs at the inner surface and the outer surface experiences the lowest degree of orientation. The gradient is nonlinear, and arises because the percent change in circumference at the inner surface is always greater than that at the outer surface.

There have been attempts to develop methods to raise the overall degree of orientation within the wall of a balloon during expansion. One method employs extruded tubing containing multiple layers of different durometers materials, with the material possessing the highest elongation (typically the lowest durometer) as the innermost layer to enable an increase in the "blow-up ratio" at the balloon's inner surface. Another method utilizes a two-stage expansion process, in which the extruded tubing is first expanded into a mold cavity of intermediate size before being subsequently expanded again into a final, larger mold. This so-called "double-blow" method helps to make the initiation event during balloon expansion less severe and enables the processing of balloons possessing a greater overall BUR value at their innermost surface.

When extruded tubing is expanded circumferentially into a balloon mold, invariably some degree of axial elongation also occurs. The actual degree of axial elongation can be calculated using measured values of initial, "as-extruded" inner diameter (ID) and outer diameter (OD), as well as the final balloon OD, and final balloon double-wall thickness. The calculated value, known as the "area draw-down ratio" (or ADDR) is the ratio of the extrusion's original cross-sectional area to the final balloon's cross-sectional area. The value of ADDR is mathematically equivalent to the ratio of the final length to the original length of the material which comprises the balloon's working length. Higher values of ADDR represent greater axial elongation during the balloon's formation.

The current design and processing approach for balloons purposely involves imparting a substantial amount of axial elongation during balloon expansion. A target ADDR value of 3.0 is common, which means that the material within the wall of the balloon's working length is stretched to 3 times its original length. This amount of axial elongation must be accounted for in the design of the extruded tubing. The extrusion's ID is already made as small as possible by the need to maximize the blow-up ratio, so it is necessary to account for the high degree of axial stretch by increasing the extrusion's OD. Geometric calculations are routinely performed to ensure that the correct final wall thickness will result when a proposed extruded tube is expanded into the desired balloon mold size with an ADDR value of about 3.0. To help control the lot-to-lot variability in axial flow behavior of the extruded tube, a specification exists for the tube's as-extruded elongation to failure (nominally 225% elongation to failure, which translates to an ADDR value of 3.25). Additionally, the amount of externally applied tension may be varied in order to help control the lot-to-lot variability in the axial elongation and thus wall thickness.

SUMMARY OF THE INVENTION

The present invention enhances a catheter balloon's performance by improving compliance and rupture properties for a given wall thickness, or by maintaining targeted balloon performance levels while reducing wall thickness. In the former instance, a balloon possessing more robust properties are made with properties similar to more non-compliant balloons with little or no loss in flexibility or deliverability. In the latter instance, either a more robust or non-compliant balloon are made thinner and thus more flexible and deliverable. Additionally, the present invention reduces the compacted or folded balloon profiles by reducing the wall thickness of balloon tapers and shafts.

The method of the invention purposely reduces the outer diameter of the as-extruded tube and correspondingly reduces the target value of ADDR during balloon expansion so that the resulting wall thickness is either unchanged (for improved balloon compliance and rupture performance without increasing wall thickness) or decreased (for comparable balloon compliance and rupture performance using thinner walls). Reducing the as-extruded tube's OD naturally raises the blow-up ratio at the outer surface of the final balloon. The blow-up ratio of underlying material within the balloon wall is also raised. The overall effect of reducing the as-extruded tube's OD is to shift the final balloon wall's BUR gradient upwards everywhere except at the innermost surface. It is further shown that a 10-20% increase in "integrated average" BUR can be attained, in theory, by the present invention. It has been confirmed experimentally that improved balloon performance, notably in rupture strength and "compliance modulus" results from the present invention.

One approach for implementing the present invention is to use a small $1^{st}$-stage mold during the double-blow process. By thus limiting the extruded tube's radial growth during the $1^{st}$ stage, the axial load imparted by the $1^{st}$ stage inflation pressure is also minimized. This is because the axial load during balloon expansion is related to the inflation pressure multiplied by the cross-sectional area of the just-formed balloon, and that small $1^{st}$ stage molds serve to minimize this cross-sectional area. By so limiting the axial elongation during the $1^{st}$ stage expansion and then transferring to a $2^{nd}$ stage mold of equivalent length, the ADDR of the final balloon after $2^{nd}$ stage can be substantially reduced. Experiments of this nature on 3.0 mm balloons have led to final ADDR values of approximately 2.0, a significant reduction from the values near 3.0 associated with conventional balloon processing.

A second approach is to controllably reduce the as-extruded tube's elongation to failure. All else being equal, extrusions possessing a high elongation to failure (say, 225% nominal, which translates to an ADDR of 3.25) naturally tend to axially elongate to a greater degree during balloon expansion than extrusions having lower elongation to failure. Thus, targeting an ADDR of 2.0 in the present invention would warrant extrusions possessing an elongation to failure more closely matched (say, 125 or 150% nominal, which translates to ADDR values of 2.25 or 2.5). In such manner, the extruded tubing would be axially deformed to an extent nearer its axial deformation limit and thus be more greatly oriented in the axial direction. The advantage of suitably reducing the as-extruded tube's elongation to failure, rather than controlling ADDR mainly through the judicious selection of $1^{st}$ stage balloon mold diameter, is that single-stage balloon expansion is possible via the former approach and the resulting ADDR during expansion tends to be self-limited by the balloon tubing.

The byproduct of reducing the as-extruded tubing's % elongation to failure is the increased likelihood of circumferential balloon ruptures, which may be addressed by modifying the balloon's post-expansion "heat set" treatment so as to promote that material change which has been shown to enhance the material's axial strength. The "enhanced heat set" approach offers the potential benefit of also increasing circumferential strength and thereby further enhancing balloon performance in terms of rupture strength and compliance modulus.

In addition, to improving performance within a balloon's working length, this invention could be also used to reduce thickness within a balloon's tapers and shafts. Consequently, a balloon's folded profile could be improved by reducing wall thickness within its tapers, which often possess the greatest profile on the larger angioplasty balloon sizes. Further, the profile of its seals could be improved by reducing wall thickness within its shafts, particularly at the proximal seal where balloon shaft drilling is not presently performed.

These and other advantages of the invention will become more apparent from the following detailed description of the invention and the accompanying exemplary drawings.

DETAILED DESCRIPTION OF THE PREFERRED EMBODIMENTS

Figure 1:
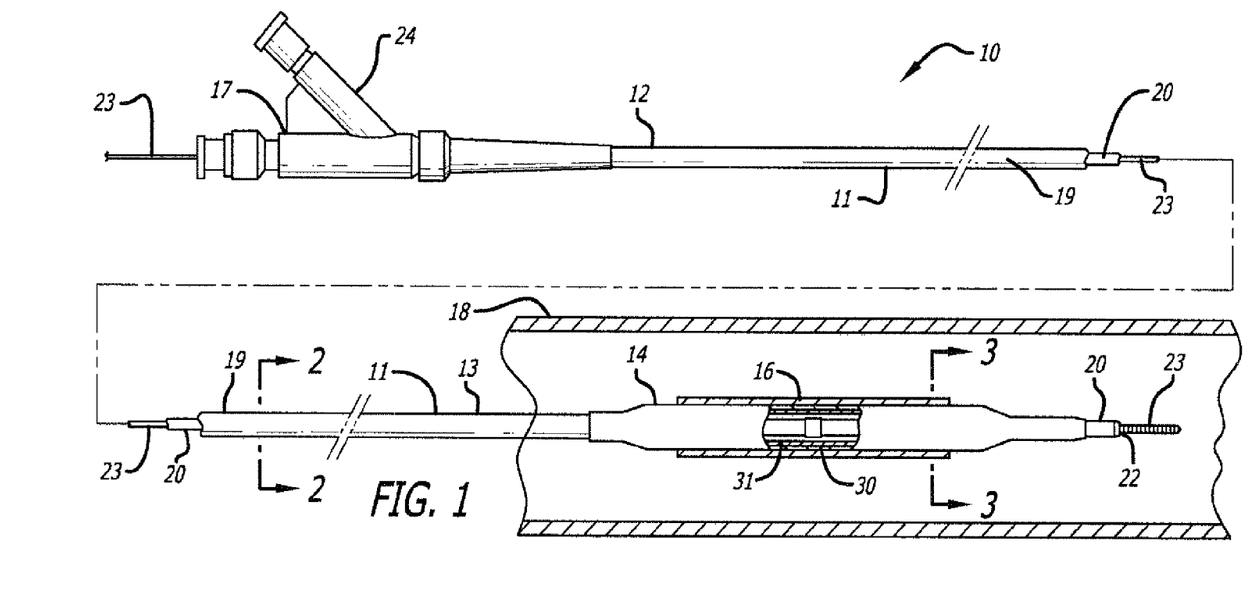
FIG. 1 is an elevational view, partially in section, of an over-the-wire type stent delivery balloon catheter embodying features of the invention.
Figure 4:
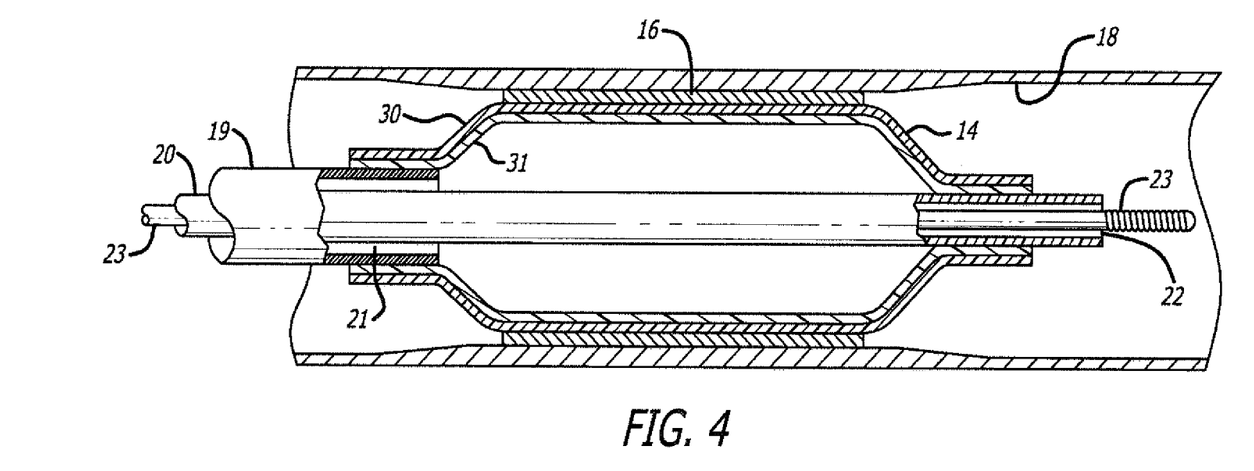
FIG. 4 illustrates the balloon catheter of FIG. 1 with the balloon inflated.

FIG. 1 illustrates a stent delivery balloon catheter 10 which embodies features of the invention, generally comprising an elongated catheter shaft 11 having a proximal shaft section 12, a distal shaft section 13, an inflation lumen 21, and a guidewire lumen configured to slidably receive a guidewire 23 therein, and having a balloon 14 mounted on the distal shaft section. An adapter 17 is on a proximal end of the catheter shaft provides access to the guidewire lumen 22, and has an arm 24 configured for connecting to a source of inflation fluid (not shown). FIG. 1 illustrates the balloon in a deflated configuration for advancement within a patient's body lumen 18. A radially expandable stent 16 is releasably mounted on the balloon for delivery and deployment within the body lumen 18. The balloon catheter 10 is advanced in the body lumen 18 with the balloon in the deflated configuration, and the balloon inflated by introducing inflation fluid into the balloon interior to expand the balloon and stent mounted thereon, and the balloon is then deflated to allow for repositioning or removal of the catheter from the body lumen 18, leaving the stent implanted in the body lumen 18. FIG. 4 illustrates the balloon catheter 10 with the balloon in the inflated configuration to expand the stent against the wall of the body lumen 18.

Figure 2:
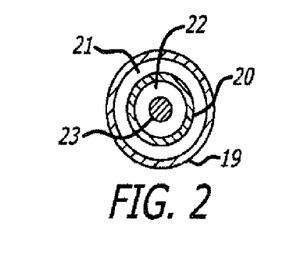
FIGS. 2 and 3 are transverse cross sectional views of the catheter of FIG. 1, taken along lines 2-2 and 3-3, respectively.
Figure 3:
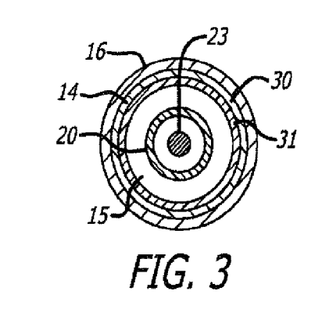

In the illustrated embodiment, the shaft comprises an outer tubular member 19 defining the inflation lumen, and an inner tubular member 20 defining the guidewire lumen 22 and positioned in the outer tubular member 19 such that the inflation lumen is the annular space between the inner surface of the outer tubular member 19 and the outer surface of the inner tubular member 20 as best shown in FIG. 2 illustrating a transverse cross section of the catheter of FIG. 1, taken along line 2-2. The balloon has a proximal skirt section sealingly secured to the distal end of the outer tubular member 19, and a distal skirt section sealingly secured to a distal end of the inner tubular member 20, so that an interior 15 of the balloon is in fluid communication with the inflation lumen 21 of the shaft. FIG. 3 illustrates a transverse cross section of the catheter of FIG. 1, taken along line 3-3, although the space between the inner surface of the deflated balloon and the outer surface of the portion of the shaft 11 therein is somewhat exaggerated for ease of illustration. A variety of alternative suitable catheter shaft configurations can be used as are conventionally known.

Although not illustrated, the balloon 14 of the invention typically has a deflated configuration with wings wrapped around the balloon to form a low profile configuration for introduction and advancement within a patient's body lumen. As a result, the balloon inflates to a nominal working diameter by unfolding and filling the molded volume of the balloon.

Balloon 14 has a first layer 30, and a second layer which is an inner layer relative to the first layer 30. In the illustrated embodiment, the second layer 31 is on an inner surface of the balloon 14 with the first layer 30 defining an outer surface of the balloon 14 and the second layer 31 defining an inner surface of the balloon 14. However, the balloon 14 of the invention can alternatively have one or more additional layers (not shown). Additional layer(s) increase the dimensions of the tube/balloon formed therefrom to a desired value, and/or can be used to provide an inner or outer surface of the balloon with a desired characteristic. Therefore, it should be understood that the balloon 14 of the invention discussed below has at least two layers, and optionally includes one or more additional layers, unless otherwise noted as having a specified set number of layers.

The first (outer) layer 30 is formed of a first polymeric material, and the second (inner) layer 31 is formed of a second polymeric material that can be expanded to a higher BUR than the first polymeric material. The second (inner) layer 31 is at a BUR which is typically about 15% to about 25% greater than the BUR of the first (outer) layer 30. Each layer 30, 31 is preferably at its maximum BUR, so that the balloon has layers of highly oriented material and, consequently, a very low compliance.

A variety of suitable materials can be used to form the first and second layers 30, 31. In a presently preferred embodiment, the first and second polymeric materials are elastomers providing a relatively low flexural modulus for balloon flexibility, although nonelastomers can alternatively be used. Presently preferred materials are from the same polymeric family/class such as polyamides including nylons and polyether block amides (PEBAX). Forming the layers of compatible polymeric materials allows for heat fusion bonding the layers together. The layers can alternatively be formed of different polymer classes which are not sufficiently compatible to fusion bond together, in which case a tie layer is typically provided between the outer and inner layers 30, 31 to bond the balloon layers together. For example, a PET inner layer and a PEBAX outer layer typically have a tie layer of an adhesive polymer such as Primacor (a functionalized polyolefin) therebetween.

The balloon 14 is formed by a method in which the layers of material that can be expanded to higher BURs are the inner layers of the balloon tubing, and lower BUR materials are the outer layers, and the balloon is blow-molded such that the innermost layer is optimized for radial orientation. By judicious selection of layer thickness, the other layer(s) can be optimized for radial orientation as well. The resulting balloon has an increased resistance to radial expansion at increasing inflation pressures.

The balloon 14 is blow-molded from a multilayered tube which has the first layer 30, and second layer 31 as an inner layer relative to the first layer 30. However, as discussed above, a balloon of the invention may have one or more additional layers, so that the tubing used to blow-mold the balloon would similarly be formed with the additional layer(s). The tube is typically formed by coextrusion, although a variety of suitable methods may be used. For example, in one embodiment, a multilayered tube is formed by coextruding at least two layers, and one or more additional layers are added to the coextruded tube by heat shrinking, adhesive or fusion bonding, or frictionally engaging the layer(s) to the coextruded tube.

Figure 5:
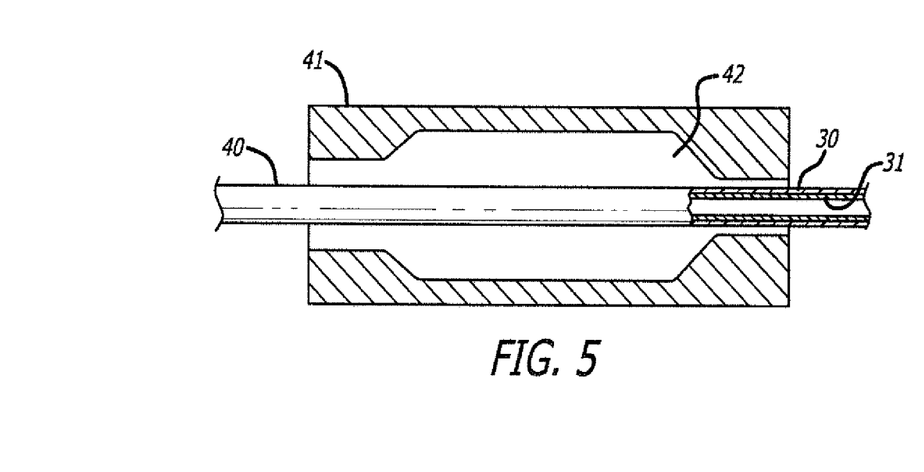
FIG. 5 is a longitudinal cross sectional view of a balloon mold, with a multilayered balloon tubing in the mold prior to being radial expanded therein.

The multilayered tube is then radially expanded in a balloon mold to form the balloon 14. FIG. 5 illustrates the multilayered tube 40 in a balloon mold 41 having an interior chamber 42 with a shape configured to form the balloon 14, and an inner diameter about equal to the nominal working diameter of the expanded balloon 14. The multilayered tube 40 is typically stretched axially and heated during blow molding in the balloon mold, as is conventionally known. For example, in one embodiment, the tube is longitudinally stretched by about 200% during blow molding, which produces a biaxially oriented balloon. The single wall thickness of the tube (prior to being radially expanded in the mold) is about 0.12 mm to about 0.5 mm, and the single wall thickness of the resulting balloon (radially expanded in the mold) is about 0.012 to about 0.050 mm, and varies depending on the desired balloon characteristics and uses.

The materials and dimensions of the multilayered tube 40 and balloon mold 41 are selected so that each layer of the balloon has been radially expanded to substantially its maximum possible amount, expressed as the BUR of the balloon layers. In a presently preferred embodiment, the outer layer 30 has a higher Shore durometer hardness than the one or more inner layers. The percentage of elongation to break of the inner layer is approximately 350%, whereas the percentage to break of the outer layer is more in the range of 220-250%. The key driver between BUR differences that can be achieved is the difference between the ultimate elongations of the material. Pebax 63D is used in a preferred embodiment as the inner layer and Pebax 70D or 72D is used as the outer layer. Pebax 63D has an elongation at break of around 350% whereas the Pebax 70D or 72D is approximately 220-250%. See U.S. Patent Publication No. 2007/0142771, incorporated herein by reference in its entirety, for further discussion of these materials.

The dimensions of catheter 10 are determined largely by the size of the balloon and guidewire to be employed, the catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), usually about 0.037 inch (0.094 cm), and the wall thickness of the outer tubular member 14 can vary from about 0.002 to about 0.008 inch (0.0051 to 0.02 cm), typically about 0.003 to 0.005 inch (0.0076 to 0.013 cm). The inner tubular member 16 typically has an inner diameter of about 0.01 to about 0.018 inch (0.025 to 0.046 cm), usually about 0.016 inch (0.04 cm), and a wall thickness of about 0.004 to about 0.008 inch (0.01 to 0.02 cm). The overall length of the catheter 10 may range from about 100 to about 150 cm, and is typically about 143 cm. Preferably, balloon 24 has a length about 0.8 cm to about 6 cm, and an inflated working diameter of about 2 to about 5 mm.

The various components may be joined using conventional bonding methods such as by fusion bonding or use of adhesives. Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 1 is an over-the-wire type stent delivery balloon catheter, the catheter of this invention may comprise a variety of intravascular catheters, such as a rapid exchange type balloon catheter. Rapid exchange catheters generally comprise a shaft having a relatively short guidewire lumen extending from a guidewire distal port at the catheter distal end to a guidewire proximal port spaced a relatively short distance from the distal end of the catheter and a relatively large distance from the proximal end of the catheter.

The present invention examines the BUR gradient of the expanded balloon as it undergoes a biaxial deformation. The extent of axial deformation occurring during balloon expansion, or Area Draw-Down Ratio ("ADDR"), is the ratio of the as-extruded tube's cross-sectional area to the balloon's as-expanded cross-sectional area. When determining the ADDR associated with a particular balloon, the calculation yields a single result. The formula for ADDR requires only the extruded material's initial OD & ID and the balloon's final OD & ID. The resulting value defines the amount of axial deformation that has occurred at every position throughout the wall of the balloon during expansion.

When calculating the BUR for a particular balloon, this also involves the material's initial and final diameters. However, the BUR formula provides a different value for every radial position within the final balloon wall. That is, for any expanded hollow cylinder, an increasing gradient in BUR from its inner surface to its outer surface will naturally occur. The precise calculation of BUR for material at any given location within a balloon wall requires that material's original radial position within the extruded tubing. Consequently, BUR values have traditionally been calculated only at the wall's inner and outer surfaces, because only there are the material's original and final radial position directly measurable or readily calculable.

Because of the unavoidable BUR gradient within the wall of any expanded balloon, it is desirable to have a single value which represents the overall extent of the circumferential deformation and thus the induced molecular orientation. The most convenient approach is to simply take the average the two BUR values corresponding to the balloon's inner and outer surfaces. However, the BUR gradient within an expanded hollow cylinder is not linear, so a simple high/low average may not be the most representative single value to describe its circumferential deformation.

A more accurate value of BUR can be determined as follows. An initial length of tubular material is internally pressurized and heated such that it expands both radially and axially into a balloon mold. Axial tension may be applied to the ends to induce additional axial deformation and thus increase ADDR, as needed. The tubular material remains pressurized while the mold is subsequently cooled. Afterward the balloon is removed from the mold cavity.

Typically the balloon's as-expanded OD is measured by laser micrometer while lightly pressurized. The balloon's double-wall thickness (DWT) is typically measured by a drop gage or snap gage when deflated. The balloon's ID can then be readily calculated by subtracting the DWT value from the OD measurement.

Figure 6:
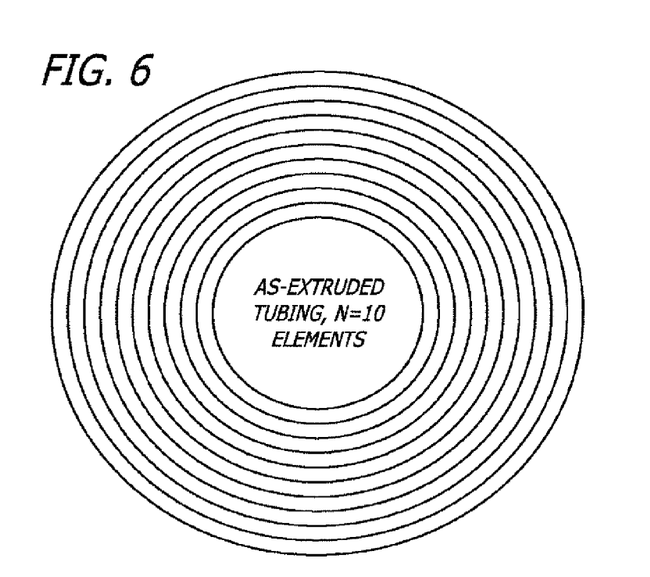
FIGS. 6 and 7 depict a tubing material's initial, as extruded dimensions prior to expansion and the tubing material's final, as expanded dimensions.
Figure 7:
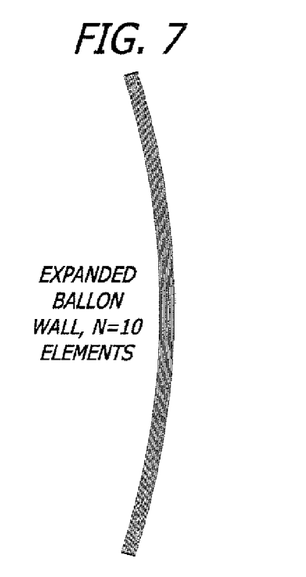

FIGS. 6 and 7 depict a representation of the tubular material's initial, as-extruded wall and the balloon's final, as-expanded wall. In each figure the wall has been divided into ten thin-walled cylindrical increments that nest within one another. As will be shown, knowing the ID's and OD's of these increments before and after expansion is the key to calculating each of their BUR values.

Definition of Variables (with Reference to FIGS. 6 and 7):
Exterior Dimensional Variables
$OD_o$=Original outer diameter of extruded material (=original outer diameter of element 1)
$ID_o$=Original inner diameter of extruded material
$L_o$=Original length of material which will be formed into a balloon
$OD_f$=Final outer diameter after balloon expansion (=final outer diameter of element 1)
$ID_f$=Final inner diameter after balloon expansion
$L_f$=Final length of the formed material after expansion
Mid-Wall Dimensional Variables
N=Number of nested, thin-walled cylindrical elements the tube is divided into
$T_o$=Original single-wall thickness of every element before expansion
$OD_{o1}(=OD_o)$=Original outer diameter of element 1
$OD_{o2}$=Original outer diameter of element 2
$OD_{o3}$=Original outer diameter of element 3
$OD_{on}$=Original outer diameter of element n
$ID_{o1}(=OD_{o2})$=Original inner diameter of element 1
$ID_{o2}(=OD_{o3})$=Original inner diameter of element 2
$ID_{o3}(=OD_{o4})$=Original inner diameter of element 3
$ID_{on}(=ID_o)$=Original inner diameter of element n
$T_{f1}$=Final single-wall thickness of element 1 after balloon expansion
$T_{f2}$=Final single-wall thickness of element 2 after balloon expansion
$T_{f3}$=Final single-wall thickness of element 3 after balloon expansion
$T_{fn}$=Final single-wall thickness of element n after balloon expansion
$OD_{f1}(=OD_f)$=Final outer diameter of element 1
$OD_{f2}$=Final outer diameter of element 2
$OD_{f3}$=Final outer diameter of element 3
$OD_{fn}$=Final outer diameter of element n
$ID_{f1}(=OD_{f2})$=Final inner diameter of element 1
$ID_{f2}(=OD_{f3})$=Final inner diameter of element 2
$ID_{f3}(=OD_{f4})$=Final inner diameter of element 3
$ID_{fn}(=ID_f)$=Final inner diameter of element n
Blow Up Ratios
$BUR_{SimpleAve}$=Average of two BUR values, at only the outer and inner surfaces
$BUR_{IntegAve}$=Average BUR, integrated across the balloon's final wall thickness
ADDR, Length Ratio, and % Elongation:

The volume of material in that span of material which participates in the balloon expansion process is conserved. For a length of hollow cylindrical material of initial length $L_o$ that elongates to some final length $L_f$:

$$(Pi/4)*(L_o)*(OD_o^2-ID_o^2)=(Pi/4)*(L_f)*(OD_f^2-ID_f^2) \text{ [constant cyl. volume]} \quad [1]$$

$$[Pi/4)*(OD_o^2-ID_o^2]/[(Pi/4)*(OD_f^2-ID_f^2)]=L_f/L_i \text{ [rearranging]} \quad [2]$$

As set forth above, Area Draw-Down Ratio, "ADDR", is defined as the ratio of final cross sectional area to original cross section area, which is the left side of Equation 2. Thus:

$$ADDR=[Pi/4)*(OD_o^2-ID_o^2)/[(Pi/4)*(OD_f^2-ID_f^2)]=L_f/L_i \text{ [definition]} \quad [3]$$

$$ADDR=(OD_o^2-ID_o^2)/(OD_f^2-ID_f^2)=L_f/L_i \text{ [simplifying]} \quad [4]$$

The right side of Equations 2, 3 and 4, here referred to as Length Ratio, is related to percent elongation as follows:

$$\% \text{ Elongation}=100*[(L_f-L_i)/L_i] \text{ [definition]} \quad [5]$$

$$\% \text{ Elongation}=100*[(L_f/L_i)-1] \text{ [rearranging]} \quad [6]$$

$$L_f/L_i=1+(\% \text{ Elongation})/100 \text{ [rearranging]} \quad [7]$$

Surface BUR Simple Average BUR Values:
By definition, the Blow Up Ratio or "BUR" is the ratio of the balloon material's final expanded diameter to its original as-extruded diameter. At the outer surface:

$$BUR_{OD}=(OD_f)/(OD_o) \text{ [definition]} \quad [8]$$

Similarly, at the inner surface:

$$BUR_{ID}=(ID_f)/(ID_o) \text{ [definition]} \quad [9]$$

[Note: $BUR_{ID}$ is sometimes estimated as $(OD_f)/(ID_o)$, because the final wall is so thin the difference between ODf and IDf is deemed negligible in this calculation.]

The "simple average" BUR is the arithmetic mean of the two surface BUR values:

$$BUR_{SimpleAve}=(BUR_{OD}+BUR_{ID})/2 \quad [10]$$

$$BUR_{SimpleAve}=[(OD_f)/(OD_o)+(ID_f)/(ID_o)]/2 \text{ [substituting Eqs. 9 \& 10]} \quad [11]$$

Original Dimensions of Thin-Walled Cylindrical Elements:

To determine the Blow-Up Ratio for a material's position somewhere within the wall of the tubing, its position must be known within both the initial extrusion and the final balloon wall. This can be done by first dividing the initial extrusion into numerous elements of the identical wall thickness. Collectively, they comprise a nested set of ultra-thin cylinders. After they have all been expanded, both in the axial and circumferential directions, to produce the balloon's final dimensions, each of their wall thickness will be thinner but no longer identical. The outermost element will have been circumferentially expanded the least amount and will therefore be thickest. Conversely, the innermost element will have been circumferentially expanded the most and will thus be thinnest. Note that the extent of the axial expansion (ADDR or Length Ratio) is the same for every element and depends only upon the expanded material's original and final lengths.

Prior to expansion, the original single-wall wall thickness ($T_o$) of every element is the as-extruded single-wall wall thickness divided by the number of elements (N):

$$T_o=[(OD_o-ID_o)/2]/N \quad [12]$$

The original OD of the outermost element ($OD_{o1}$) is identical to the original outer diameter of the extruded material ($OD_o$). The original ID of the element ($ID_{o1}$) is, of course, less than OD by its double-wall thickness:

$$OD_{o1}=OD_o \quad [13]$$

$$ID_{o1}=OD_o-2*T_o \quad [14]$$

The original OD of the next element inward ($OD_{o2}$) is the same as the original ID of the previous element ($ID_{o1}$). Its original ID is, again, less than its OD by its double-wall thickness:

$$OD_{o2}=ID_{o1} \quad [15]$$

$$ID_{o2}=OD_{o2}-2*T_o \quad [16]$$

Similar formulas apply for all subsequent elements. For the innermost element:

$$OD_{on}=ID_{o(n-1)} \quad [17]$$

$$ID_{on}=OD_{on}-2*T_o=ID_o \quad [18]$$

Final Dimensions of Thin-Walled Cylindrical Elements:

The final OD of the outermost element ($OD_{f1}$) is identical to the final balloon OD ($OD_f$) so it is directly measurable after expansion. The final ID of this element can be calculated based on its original OD and ID, its final OD, and the Area Draw-Down Ratio. The pertinent formula is the same as Equation 4:

$$ADDR = (OD_{o1}^2 - ID_{o1}^2)/(OD_{f1}^2 - ID_{f1}^2) \text{ [customization of Eq. 4]}$$

$$(OD_{f1}^2 - ID_{f1}^2) = (OD_{o1}^2 - ID_o^2)/ADDR \text{ [rearranging]}$$

$$ID_{f1}^2 = OD_{f1}^2 - (OD_{o1}^2 - ID_{o1}^2)/ADDR \text{ [rearranging]}$$

$$ID_{f1} = [OD_{f1}^2 - (OD_{o1}^2 - ID_{o1}^2)/ADDR]^{1/2} \text{ [rearranging]}$$

$$ID_{f1} = [OD_f^2 - (OD_o^2 - ID_{o1}^2)/ADDR]^{1/2} \text{ [substituting Eq. 13]} \qquad [19]$$

Equation 19 gives the final ID of the 1$^{st}$ element in terms of the tube's original and final outside diameter, the original ID of that element, and the ADDR. The formula for calculating the final ID of the 2$^{nd}$ element is similar to equation 19. However, because all elements are nested both before and after expansion, the final OD of the 2$^{nd}$ element ($OD_{f2}$) is identical to the final ID of the 1$^{st}$ element ($ID_{f1}$), and the original OD of the 2$^{nd}$ element ($OD_{o2}$) is identical to the original ID of the 1$^{st}$ element ($ID_{o1}$). Making appropriate substitutions into Equation 19 yields:

$$ID_{f2} = [ID_{f1}^2 - (ID_{o1}^2 - ID_{o2}^2)/ADDR]^{1/2} \qquad [20]$$

Similar formulas can be used to calculate the final ID's of all remaining elements. For the innermost element, note that the original ID is $ID_o$ and the final ID is $ID_f$.

$$ID_{fn} = [ID_f^2 - (ID_{o(n-1)}^2 - ID_o^2)/ADDR]^{1/2} \qquad [21]$$

Interior BUR Values:

Using the final ID values calculated using Equations 19 and 20, and the original ID values calculated via the examples provided by Equations 14 and 16, the Blow Up Ratio for any element, regardless of its position, can be calculated as follows:

$$BUR_1 = ID_{f1}/ID_{o1} \text{ [definition of BUR]} \qquad [22]$$

$$BUR_2 = ID_{f2}/ID_{o2} \text{ [definition of BUR]} \qquad [23]$$

$$BUR_n = ID_{fn}/ID_{on} \text{ [definition of BUR]} \qquad [24]$$

Integrated Average BUR:

Because Blow Up Ratio varies from one element to another, with the highest value at the inner surface and the lowest at its outer surface, when BUR is plotted vs. position within the balloon's final wall a curve is produced. Finding the area under this curve enables an "integrated average" BUR value to be obtained. The area under the curve is readily calculated by numerical integration. This involves multiplying each element's BUR by its final wall thickness and summing:

$$\text{Area Under Curve} = \Sigma[BUR_1*(OD_f - ID_{f1})/2] + [BUR_2*(OD_{f2} - IF_{f2})/2] + \ldots [BUR_n*(OD_{fn} - ID_{fn})/2] \qquad [25]$$

It turns out that every individual product of BUR*thickness (each bracketed term in equation 25) approaches the same numerical value as the number of elements is increased. This is because any element's final thickness is inversely proportional to its extent of circumferential strain, whereas its Blow Up Ratio is directly proportional to circumferential strain; the change in one value balances the change in the other. To calculate the area under the curve, it is therefore only necessary to compute the BUR and final thickness for one element, calculate their product, and then multiply this product by the number of elements. The outermost element is the obvious choice in this endeavor, because its original and final OD are directly measurable. Thus:

$$\text{Area Under Curve} = N*[BUR_1*(OD_f - ID_{f1})/2] \qquad [26]$$

Substituting equation 22 in equation 26 produces:

$$\text{Area Under Curve} = N*[(ID_{f1}/ID_{o1})*(OD_f - ID_{f1})/2] \qquad [27]$$

$$\text{where } ID_{f1} = [OD_f^2 - (OD_o^2 - ID_{o1}^2)/ADDR]^{1/2} \qquad [Eq. 19]$$

$$\text{and } ID_{o1} = OD_o - 2*T_o \qquad [Eq. 14]$$

$$\text{and } T_o = [(OD_o - ID_o)/2]/N \qquad [Eq. 12]$$

For any numerical integration, the accuracy tends to improve as the number of elements increases. Due to the convenient simplification represented in equation 26 or 27, the number of terms that must be computed and summed does not depend on the number of elements. Thus, there is no workload penalty for selecting as many as 100, or even 1000 elements to improve accuracy.

The area under the curve obtained via equation 26 or 27 happens to be in units of BUR*in or BUR*mm, depending on the unit of measure used for diameter. Dividing the area under the curve by the balloon's final single-wall thickness results in an "integrated average" BUR value that is dimensionless. Thus:

$$BUR_{IntegAve} = N*[BUR_1*(OD_f - ID_{f1})/2]/(OD_{f1} - ID_{f1})/2] = N*BUR_1 \qquad [28]$$

$$BUR_{IntegAve} = N*[ID_{f1} - ID_{o1})] \qquad [29]$$

$$\text{where } ID_{f1} = [OD_f^2 - (OD_o^2 - ID_{o1}^2)/ADDR]^{1/2} \qquad [Eq. 19]$$

$$\text{and } ID_{o1} = OD_o - 2*T_o \qquad [Eq. 14]$$

$$\text{and } T_o = [(OD_o - ID_o)/2]/N \qquad [Eq. 12]$$

Figure 8:
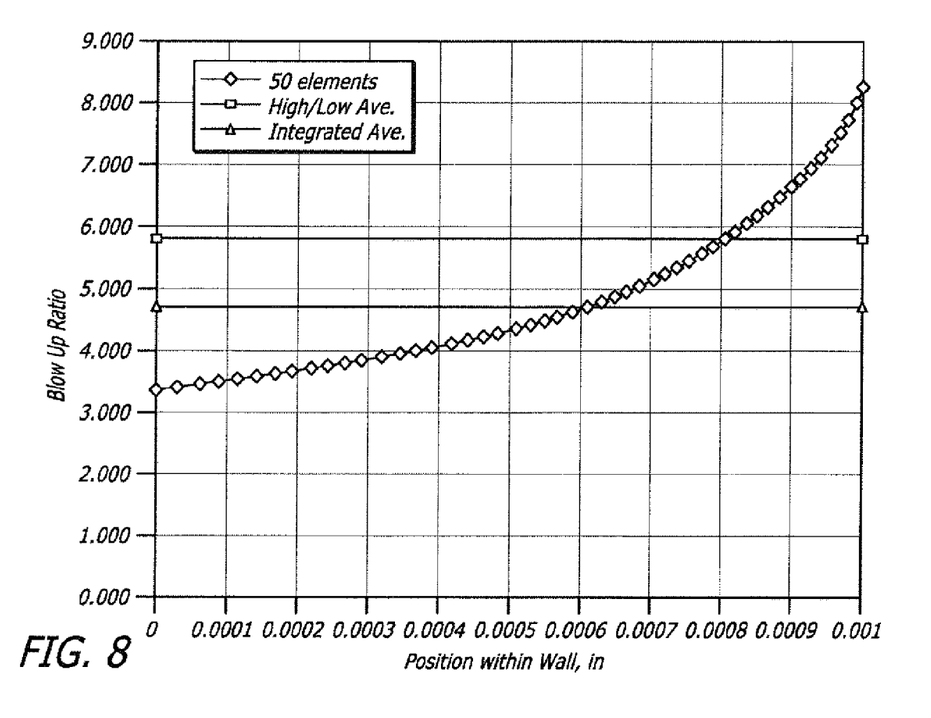
FIG. 8 is a plot of Blow Up Ratio as a function of position within the balloon wall after expansion.
Figure 9:
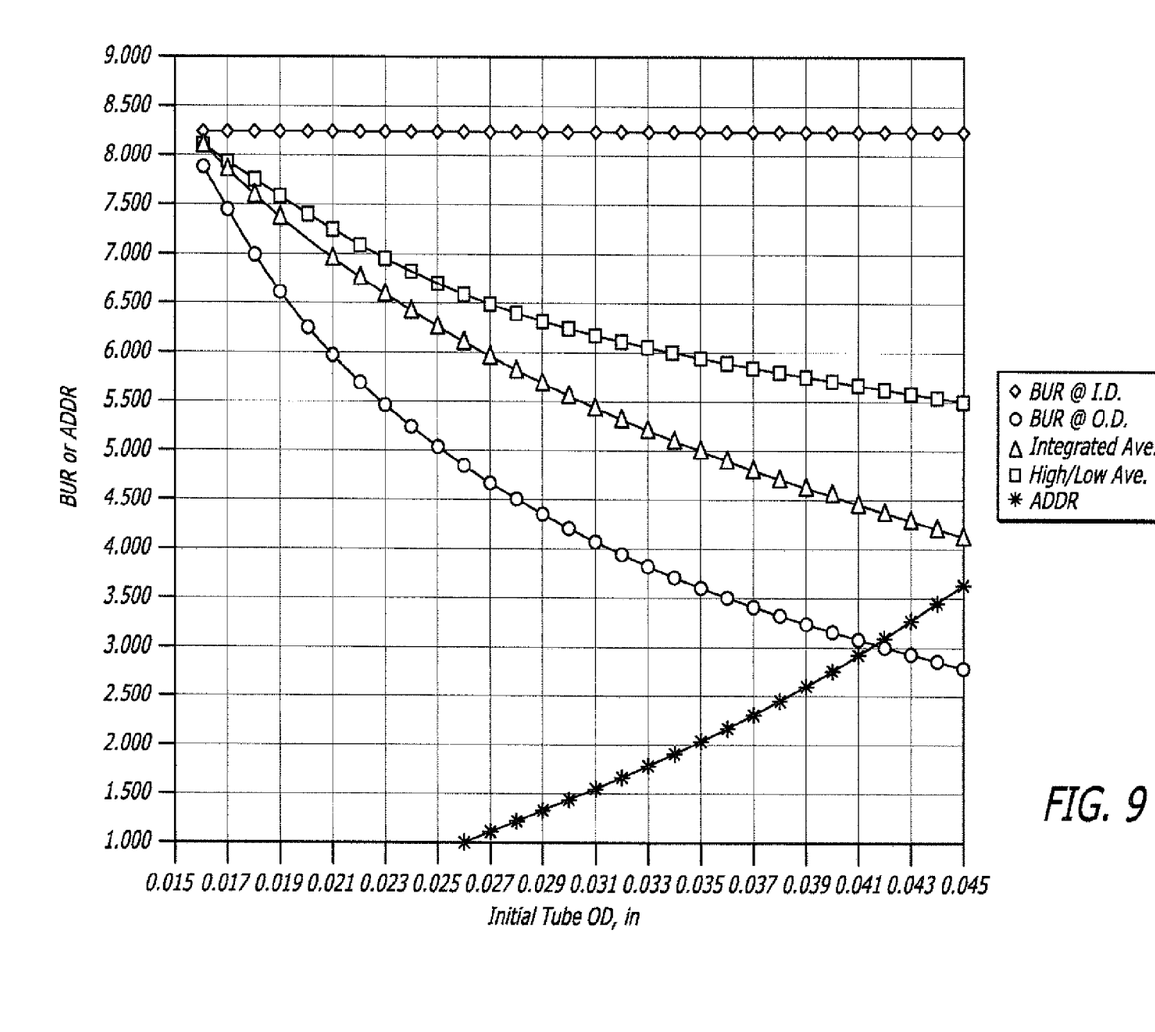
FIG. 9 is a plot of BUR and ADDR as a function of initial tube OD.

Due to the nature of the curve of BUR vs. position within a balloon's final wall thickness (concave upward), the value of $BUR_{IntegAve}$ will always be less than the value of $BUR_{SimpleAve}$. FIG. 8 illustrates the nonlinear gradient in BUR within the wall of a balloon. The integrated average BUR is clearly less than the simple "high/low" average BUR value. The disparity between these values depends upon the initial tubing dimensions and the associated ADDR. FIG. 9 graphically depicts this relationship. Here the original extrusion's ID is fixed at 0.015", while its OD varies along the horizontal axis. The balloon's final ID and OD are also fixed, at 0.123"×0.125", which means that the ADDR must vary as shown in FIG. 9.

Note that the "integrated average" BUR is always less than the simple "high/low" average BUR, but that they increase and become closer together as the initial tube OD is decreased and the ADDR is correspondingly reduced. Thus, in order to raise the extent of the circumferential orientation throughout the balloon wall and, consequently, to reduce balloon compliance and increase rupture strength, the as-extruded tube OD should be reduced and the ADDR correspondingly diminished. In effect, this would raise circumferential orientation at the expense of axial orientation. However, there is a practical limit: an ADDR below 1.0 means that the material must be axially compressed during expansion, which seems unlikely if not impossible by traditional methods.

However, blowing the balloon in two multiple stages ("double blow") allows the overall ADDR to be reduced and thus enable the use smaller as-extruded OD's. This, of course, would also help to reduce wall thickness within balloon tapers and balloon shafts.

EXAMPLE

A variety of experiments have been performed using 3.0 mm $2^{nd}$ stage balloon molds, dual-layer balloon tubing (Pebax 63D inner, Pebax 72D outer) and the double-blow process with various $1^{st}$-stage balloon mold sizes. The highest degree of success is attained by extruding balloon tubing to the same ID as conventional tubing, but with a smaller OD, and correspondingly reducing the area draw down ratio (ADDR) resulting from a $2^{nd}$ stage balloon expansion so that the wall thickness within the working length matches that of a conventional 3.0 mm balloon.

The target range for % elongation to failure of conventional as-extruded balloon tubing (ca. 225%) does not work well for the present invention. Consequently, the actual ADDR's resulting from $2^{nd}$ stage balloon expansion were too high in initial experiments, which led to inadequate wall thickness and abnormally low rupture values. However, analysis of the balloon compliance test data showed that, despite undesirably low ruptures, these balloons exhibited unusually high values of compliance modulus (the rate of change of hoop stress with respect to the change in hoop strain as balloon inflation pressure is ramped upward). For a given balloon size and double-wall thickness, higher compliance modulus values are generally associated with flatter balloon compliance curves and higher rupture strengths.

Next, the target % elongation to failure of as-extruded tubing was reduced so that less axial stretch would naturally occur during balloon expansion, thereby lowering the actual ADDR and increasing the final balloon wall thickness so that it matched that of conventional 3.0 mm balloons. This had the desired effect of raising the rupture strength, to the extent that the mean rupture strength and rated burst pressure (RBP), when normalized for wall thickness, exceeded that of conventional 3.0 mm balloons. However the majority of samples failed circumferentially (radial rupture) rather than longitudinally (axial rupture). For product safety reasons, it is much preferred that balloon ruptures in the longitudinal direction, and the majority of conventionally-processed balloons fail in the longitudinal mode.

Figure 10:
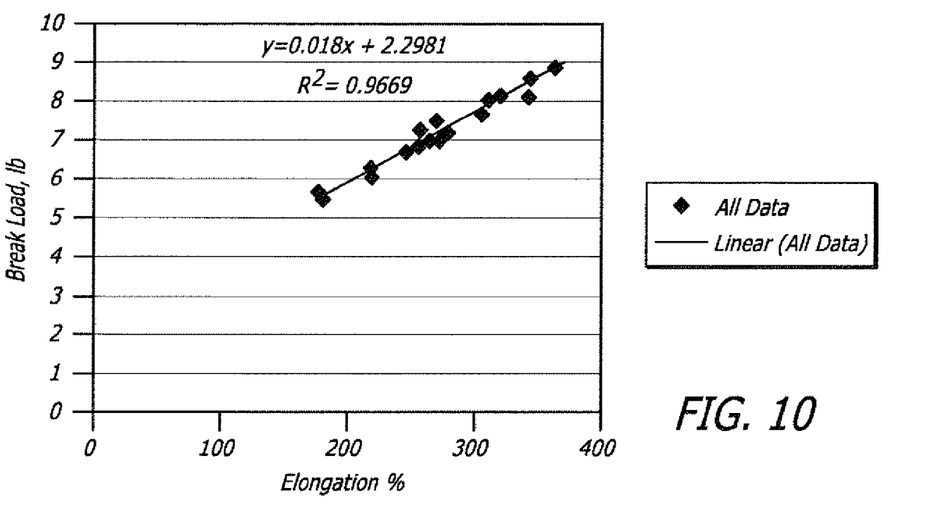
FIG. 10 is a plot of average tensile break load versus average percent elongation for a variety of Pebax 72 balloon tubing lots purposely processed to have different average percent elongation values.

To pinpoint the reason for the change in balloon rupture mode, previous balloon tubing tensile test data was analyzed. The tensile data represented nineteen different Pebax 72d balloon tubing extrusion runs involving various puller speeds, air gap distances, melt temperatures, and draw-down ratios. The groups exhibited a variety of average % elongation values, as expected. The trend is depicted graphically in FIG. 10. It was initially assumed that those combinations of extrusion parameters which increase the rate of cooling from the melt would cause the material to retain a greater degree of axial alignment, thereby reducing the tubing's % elongation to failure and increasing its tensile break load. However, as the % elongation decreased, so did the tensile break load.

The observed decrease in tensile break load with increasing rate of cooling from the melt is possibly caused by the higher cooling rates inhibiting crystallization within the material's "hard" segments. Pebaxes are block copolymers comprised of largely amorphous "soft" segments interspersed with semi-crystalline "hard" segments. Thus, a more rapid cooling rate during extrusion lowered the % elongation via enhanced axial orientation within both segment types, but may have lowered the overall tensile strength by reducing the percent crystallinity primarily within the hard segment. Heating the extruded material to temperatures below but near the melting point enhances molecular mobility and enables additional crystallization to occur, thereby raising the tensile strength.

Figure 11:
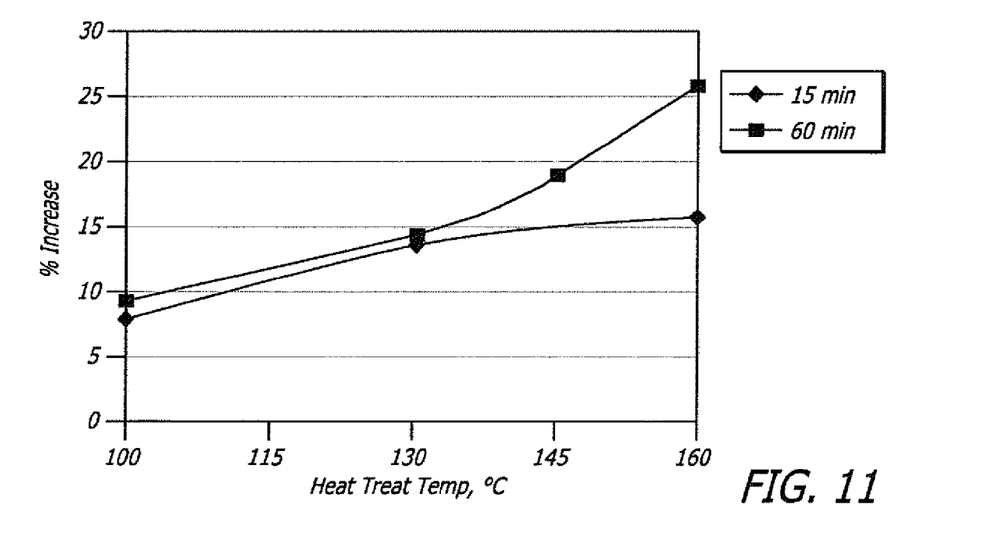
FIG. 11 is a plot of heat treat temperature versus percentage increase in balloon break load.

This was supported by heat treating low-elongation dual-layer balloon tubing at various temperatures ranging from 100° C. to 160° C. for times of 15 and 60 minutes. FIG. 11 shows that the tensile break load is increased by up to 25% or more simply through post-extrusion heat treatment. The various heat treatments had virtually no impact on the tubing's % elongation to failure. It was thought that the observed increase in tensile break load would serve to reduce or altogether eliminate the tendency for balloons made from this tubing to rupture in the undesirable circumferential failure mode. Attempts to process balloons from the tubing after various heat treatments were largely unsuccessful. Those groups which could be processed at all had narrow process windows and low yields, and often exhibited cosmetic defects. In short, heat treating to raise tensile strength prior to balloon expansion dramatically reduced the extruded material's processability during balloon blow.

Efforts to reduce or eliminate circumferential ruptures involve heat treatments that are similar but are performed after balloon expansion. For example, balloons subject to a heat set heat treatment at approximately 60° C. for about fifteen minutes while lightly pressurized to preserve dimensions. That time/temperature combination is thought to be insufficient to bring about substantial improvement in axial strength. Higher temperatures and longer times have brought about a boost in axial strength comparable to as-extruded balloon tubing. It has been found that radial containment of the balloons is preferable so their diameters do not creep to unacceptably large values during the requisite heating and pressurization.

The byproduct of reducing the as-extruded tubing's % elongation to failure is the increased likelihood of circumferential balloon ruptures, which may be addressed by modifying the balloon's post-expansion "heat set" treatment so as to promote that material change which has been shown to enhance the material's axial strength. The "enhanced heat set" approach offers the potential benefit of also increasing circumferential strength and thereby further enhancing balloon performance in terms of rupture strength and compliance modulus.

In addition, to improving performance within a balloon's working length, this invention could be also used to reduce thickness within a balloon's tapers and shafts. Consequently, a balloon's folded profile could be improved by reducing wall thickness within its tapers, which often possess the greatest profile on the larger angioplasty balloon sizes. Further, the profile of its seals could be improved by reducing wall thickness within its shafts.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed:
1. A method of making a balloon for a catheter comprising:
   providing a multilayer tube comprising a first layer of a first elastomeric polymeric material and a second layer of a second elastomeric polymeric material, the second elastomeric polymeric material having a lower maximum blow up ratio (BUR) than the first elastomeric polymeric material, and the multilayer tube having an inner diameter and an outer diameter, wherein the second layer is an outer layer relative to the first layer; and forming a multilayer balloon by blow-molding the multilayer tube such that the multilayer balloon is blown, in at least a first stage, to a final working radial dimension, wherein an area draw-down ratio (ADDR) of 2.0 for the multilayer balloon is targeted.

2. The method of claim 1, wherein the second elastomeric polymeric material has a Shore durometer hardness greater than a Shore durometer hardness of the first elastomeric polymer material.

3. The method of claim 1, wherein the multilayer tube is formed by coextrusion.

4. The method of claim 1, wherein the first layer is bonded to the second layer with a tie layer.

5. The method of claim 1, wherein the balloon catheter is a stent delivery catheter, and further wherein an expandable stent is mounted on the multilayer balloon for delivery and deployment within a patient's body lumen.

6. The method of claim 1, wherein the multilayer balloon is blown in the first stage to a first radial dimension, and further wherein the multilayer balloon is blown in a subsequent stage to the final working radial dimension.

7. The method of claim 1, further comprising heating the balloon to at least 100° C. for about fifteen to about sixty minutes after blow-molding.

8. The method of claim 1, wherein the multilayer balloon is blown in the first stage to the final working radial dimension, and further wherein the multilayer balloon is heat set at a temperature above 100° C. after blow molding.

9. The method of claim 8, wherein the multilayer balloon is heat set for about 15 to about 60 minutes.

10. The method of claim 8, wherein the second layer has a Shore durometer hardness greater than a Shore durometer hardness of the first layer.

11. The method of claim 8, wherein the first layer is bonded to the second layer with a tie layer.

12. The method of claim 8, wherein the balloon catheter is a stent delivery catheter, and further wherein an expandable stent is mounted on the multilayer balloon for delivery and deployment within a patient's body lumen.

13. The method of claim 1, wherein the multilayer balloon has an average blow up ratio (BUR) greater than that of a comparative multilayer balloon having a first layer of the first elastomeric polymeric material and a second outer layer of the second elastomeric polymeric material and wherein an area draw-down ratio (ADDR) of 3.0 for the comparative multilayer balloon is targeted.

14. The method of claim 13, wherein the average blow up ratio is an integrated average blow up ratio.

15. The method of claim 1, wherein the multilayer balloon has a circumferential orientation throughout a balloon wall greater than that of a comparative multilayer balloon having a first layer of the first elastomeric polymeric material and a second outer layer of the second elastomeric polymeric material and wherein an area draw-down ratio (ADDR) of 3.0 for the comparative multilayer balloon is targeted.

16. The method of claim 1, wherein the multilayer balloon has a compliance less than that of a comparative multilayer balloon having a first layer of the first elastomeric polymeric material and a second outer layer of the second elastomeric polymeric material and wherein an area draw-down ratio (ADDR) of 3.0 for the comparative multilayer balloon is targeted.

17. The method of claim 1, wherein the multilayer balloon has a rupture strength greater than that of a comparative multilayer balloon having a first layer of the first elastomeric polymeric material and a second outer layer of the second elastomeric polymeric material and wherein an area draw-down ratio (ADDR) of 3.0 for the comparative multilayer balloon is targeted.

18. The method of claim 1, wherein the multilayer balloon is formed by blowing molding an extruded tube, the extruded tube having an elongation to failure between about 125% and about 150%.

* * * * *